Figure 1:
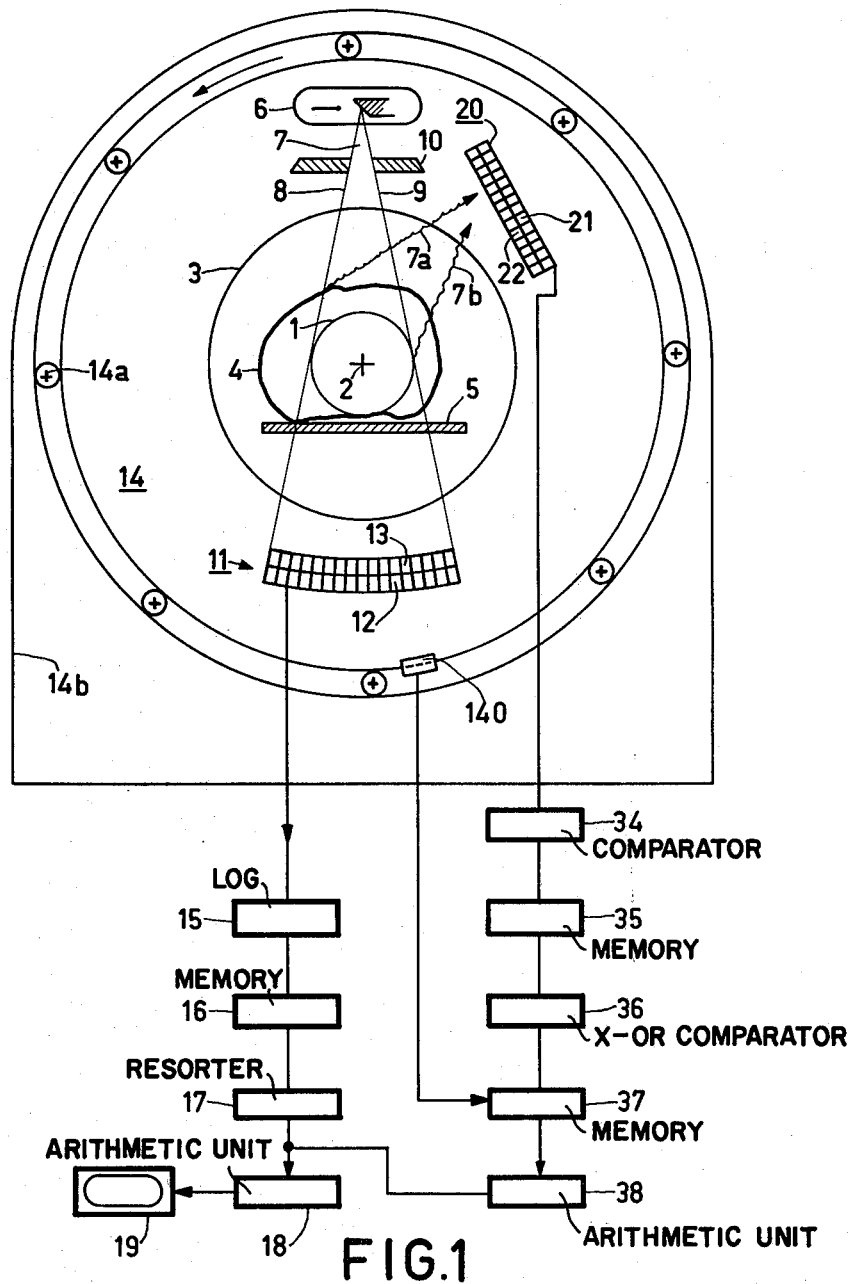

United States Patent [19]

Wagner et al.

[11] 4,384,209

[45] May 17, 1983

[54] METHOD OF AND DEVICE FOR DETERMINING THE CONTOUR OF A BODY BY MEANS OF RADIATION SCATTERED BY THE BODY

[75] Inventors: Wolfgang Wagner, Hamburg; Geoffrey Harding, Rellingen, both of Fed. Rep. of Germany

[73] Assignee: U.S. Philips Corporation, New York, N.Y.

[21] Appl. No.: 164,109

[22] Filed: Jun. 30, 1980

[30] Foreign Application Priority Data

Jun. 30, 1979 [DE] Fed. Rep. of Germany ......... 292645

[51] Int. Cl.³ .............................................. A61B 6/00
[52] U.S. Cl. ...................................... 378/14; 364/414
[58] Field of Search ..................... 250/445 T; 364/414

[56] References Cited

U.S. PATENT DOCUMENTS

| | | | |
|---|---|---|---|
| 3,106,640 | 10/1963 | Oldendorf | 250/445 T |
| 3,927,318 | 12/1975 | Macovski | 250/445 T |
| 4,124,804 | 11/1978 | Mirell | 250/445 T |
| 4,228,505 | 10/1980 | Wagner | 364/414 |
| 4,277,686 | 7/1981 | Harding | 250/445 T |

*Primary Examiner*—Alfred E. Smith
*Assistant Examiner*—T. N. Grigsby
*Attorney, Agent, or Firm*—Jack E. Haken

[57] ABSTRACT

When only a part of a body slice to be examined, for example, a separate organ, is irradiated by means of a fan-shaped radiation beam during computer tomography, it is necessary to know the body contour in order to enable reconstruction. The body contour can be determined by means of radiation scattered in the body. The scattered radiation is measured, in a direction which deviates from the direction of the X-rays of the fan-shaped beam, along scattered radiation paths which do not intersect each other in the positioning zone. On the basis of the detected scattered radiation, the scattered radiation path which is situated most far from the center of the examination zone is selected, after which the position of the scattered radiation path within the fan-shaped radiation beam, and hence within the positioning zone, is recorded. After the recording of all scattered radiation paths for the different directions of the fan-shaped radiation beam, the contour of the body slice to be examined is determined from the recorded positions of the scattered radiation paths.

17 Claims, 5 Drawing Figures

METHOD OF AND DEVICE FOR DETERMINING THE CONTOUR OF A BODY BY MEANS OF RADIATION SCATTERED BY THE BODY

The invention relates to a method of determining the contour of a body in order to reconstruct the absorption distribution of radiation in a flat examination zone of the body, the examination zone being situated within a positioning zone which encloses the examination zone and in which the body is positioned. The examination zone is completely irradiated from different directions in the examination plane by means of a fan-shaped radiation beam in order to determine measuring values. For each direction of the fan-shaped radiation beam auxiliary radiation is measured which is influenced by the body and which extends outside the radiation beam and possibly in the plane of examination in order to determine contour points of the body wherefrom the absorption distribution is reconstructed in conjunction with the measuring values. The invention furthermore relates to a device for performing the method.

During the measurement in most prior art computer tomography apparatus, a system formed by a radiation source and a detector device is rotated around an axis which extends perpendicularly to the examination plane in order to record transmission measuring values, thus defining the examination zone as a circular zone which is concentrically situated with respect to the axis and which is irradiated by a fan-shaped radiation beam from the radiation source in any position of the system formed by the radiation source and the detector device.

A body slice whose absorption distribution is to be reconstructed, therefore, is positioned completely within the examination zone, so that there is no part of the slice wherefrom measuring values cannot be obtained in all measuring direction (because it is situated outside the examination zone). Otherwise, large errors occur during the subsequent reconstruction of the absorption distribution in the examination zone. The examination zone, therefore, should as a rule be so large that bodies of particularly large dimensions at the area to be examined can be positioned completely within the examination zone.

However usually only a limited image zone is of importance for the diagnosis, for example, an organ within the human body. Therefore, it is desirable to limit the recovery of measuring values to this limited zone, because the radiation dose administered to the patient is thus also limited.

The previous German Patent Application P 28 02 593.6 describes a method of determining the spatial distribution of the absorption of radiation which enables reconstruction of the absorption distribution in the examination zone also when the body contour is situated completely outside the examination zone.

This method is based on the determination of the contour of a body as an envelope of light rays which are tangent to the body and which extend in the examination plane, an optical scanning system being used to scan the body contour situated outside the examination zone. However, only a convex contour of the body can be determined by means of envelopes, so that errors occur when the contour comprises, for example, concave sections. Moreover, this method not only requires the customary X-ray source, but also an additional auxiliary radiation source and detector for emitting and detecting respectively the light rays.

The invention has for its object to provide a method of determining the contour of a body for the reconstruction of the absorption distribution in a plane of the body and also a device for performing the method by means of which convex as well as concave sections of the body contour can be determined, without auxiliary radiation sources being required.

To this end, a first method in accordance with the invention is characterized in that X-rays which extend in a direction other than that of the X-rays of the fan-shaped radiation beam and which are scattered by the body are measured as auxiliary radiation along scattered radiation paths, which do not overlap in the positioning zone and which cover at least approximately one half of the positioning zone adjacent a centre situated therein, after which from the number of scattered radiation paths the path is selected which is situated most far from the centre of the examination zone and along which scattered radiation has been measured, the position within the positioning zone of a segment of the selected scattered radiation path which extends within the fan-shaped radiation beam being recorded, whilst after the recording of the positions of all path segments for the different directions of the fan-shaped radiation beam there are determined points of intersection of the path segments and straight lines which pass through the centre, said lines enclosing a small angle with respect to each other and the lines together being fan-shaped to an angle of 180°, the points of intersection which are situated at the shortest distance from the centre being recorded as contour points.

A second method in accordance with the invention is characterized in that the X-rays which are scattered by the body in a measuring plane, which contains a beam path of the fan-shaped radiation beam and which encloses an angle with respect to the examination plane, are measured as the auxiliary radiation, scattered radiation from adjacent points on the beam path being stopped so that an unambiguous relationship is established between the adjacent points on the beam path and adjacently extending scattered radiation paths which extend through said adjacent points, a contour point being determined by comparison of output signals which are obtained by detection of scattered radiation along the adjacently extending scattered radiation paths.

The invention is based on the fact that a satisfactory determination of the absorption distribution in the examination zone can be realized if for the unknown measuring values on beam paths extending outside the examination plane, use is made of geometrical length values which are to be multiplied by a mean value of the body absorption. To this end, the body contour must at least be approximately known. Subsequently, the geometrical length values are calculated as the distance between the points of intersection of straight lines outside the examination zone and the body contour. The determination of the absorption in the examination zone by means of the measuring values obtained during irradiation of the examination zone and the geometrical length values multiplied by the mean body absorption has been experimentally tested with success (see the contribution in Medita, Special Issue I/78, Basel, 1978).

The invention is also based on the fact that a part of the X-radiation penetrating the body is scattered laterally with respect to the fan-shaped radiation beam by the Compton effect and is detected by means of an auxiliary detector device which is arranged to be stationary with respect to the fan-shaped radiation beam and which thus participates in the rotation of the system formed by the radiation source and the detector device. When the scattered radiation is detected along suitably selected scattered radiation paths, for example, along scattered radiation paths which extend parallel to each other in the examination plane and which almost fully cover the positioning zone, scattered radiation is detected along the scattered radiation paths which extend through the body. The scattered radiation occurring along the scattered radiation paths which extend outside the body is very small in comparison therewith. By the sampling of the detector output signals, the scattered radiation path is determined on which the presence of scattered radiation was clearly established and which is situated most far from the centre of the examination zone. This scattered radiation path has a path segment which corresponds as regards position and size to the part of the scattered radiation path which is situated within the fan-shaped radiation beam and which starts from the body or is tangent thereto. A large number of such path segments are thus used for determining contour points of the body by determination of the points of intersection of vectors (straight lines) which extend from the centre of the examination zone in different polar directions and the radiation path segments. Thus, a path segment is associated with each direction of the fan-shaped radiation beam. On each vector the point of intersection which is situated most near to the centre is then assigned to be a contour point of the body. In addition to the determination of contour points on convex body contours, this method also enables determination of contour points in a concave part of a contour of the body. The result of the method is more accurate as the angle of aperture of the fan-shaped radiation beam is smaller. Use is made only of the X-rays scattered by the body, so that no additional auxiliary radiation sources are required.

It is also possible to detect the scattered X-rays also along scattered radiation paths which are situated in a measuring plane which contains one beam path of the fan-shaped radiation beam and which encloses an angle with respect to the examination plane. For example, this single beam path may be the symmetry line or one of the extreme rays of the fan-shaped radiation beam. Such a beam path extends through the focus of the radiation source and a separate detector of the detector device. When a beam path thus selected is imaged, for example, by means of diaphragms, on a detector device situated in this measuring plane, or in other words when each point on the beam path is unambiguously associated with a given part of the detector device, for each direction of the fan-shaped radiation beam or the selected beam path one contour point of the body can be determined by comparison of the scattered radiation along neighbouring scattered radiation paths, thus by comparison of the corresponding detector output signals. A contour point is then the point of intersection of the scattered radiation path and the beam path of the fan-shaped radiation beam on which a sufficient amount of scattered radiation is measured and which is situated most far from the centre of the examination zone. Thus, contour points can be accurately determined in concave parts of the body contour again without auxiliary radiation sources being necessary.

An embodiment of a device in accordance with the invention for performing the described method comprises a radiation source which is mounted on a rotatable support and which emits a fan-shaped radiation beam in order to irradiate a flat examination zone of the body, there being provided a positioning zone for a body which is larger than the examination zone and which encloses the examination zone, a detector device which is arranged opposite the radiation source for determining measuring values, and an auxiliary detector device which consists of separate detector elements which are adjacently arranged in the plane of examination and which measures auxiliary radiation which extends outside the radiation beam and within the plane of examination and which is to be influenced by a body in order to determine contour points of the body wherefrom, together with the measuring values, a two-dimensional absorption distribution of the body can be reconstructed by means of a first electronic unit, and is characterized in that in front of each detector element of the auxiliary detector device on the rotatable support for the detection of the X-rays scattered by the body there is provided a collimator for stopping scattered radiation paths whose direction deviates from the direction of the X-rays in the fan-shaped beam, at least one half of the positioning zone adjacent a centre situated therein being covered by adjacent scattered radiation paths, the separate detector elements being connected to an electronic unit for determining the contour points of the body from the output signals of the detector elements.

Said auxiliary detector device, whose individual detector elements are provided each with a collimator, simply defines or stops scattered radiation paths which extend in the examination plane and which cover at least approximately one half of or the complete positioning zone. During the determination of the measuring values, the scattered radiation paths covering the positioning zone are placed in any angular position required for determining different contour points by rotation of the support on which the auxiliary detector device is mounted.

A further embodiment of a device in accordance with the invention for performing the method comprises a radiation source which is mounted on a rotatable support and which emits a fan-shaped radiation beam for irradiating a flat examination zone of a body, there being provided a positioning zone for a body which is larger than the examination zone and which encloses the examination zone, a detector device which is arranged opposite the radiation source for determining measuring values, and an auxiliary detector device which measures auxiliary radiation which extends outside the radiation beam and which is to be influenced by a body in order to determine contour points of the body wherefrom, in conjunction with the measuring values, a two-dimensional absorption distribution of the body can be reconstructed by means of an electronic unit, is characterized in that in front of the auxiliary detector device there is arranged a first diaphragm device so that only scattered radiation which extends in a measuring plane reaches the auxiliary detector device, said measuring plane enclosing an angle with respect to the examination plane, one beam path being situated in the measuring plane and in the examination plane there being provided a second diaphragm device for admitting a desirable part of the scattered radiation extending in the measuring plane to the auxiliary detector device which is connected to an electronic unit for determining the contour points of the body from the output signals of the auxiliary detector device.

By means of the said auxiliary detector device and the first and second diaphragm devices it is achieved that the scattered radiation originating from the selected beam path of the fan-shaped radiation beam and extending in the measuring plane is measured on the auxiliary detector device along defined scattered radiation paths. The complete as well as half the beam path situated within the positioning zone can be considered in this respect. After each rotation of the support on which the auxiliary detector device and the diaphragm devices are mounted, the beam path of the fan-shaped radiation beam intersects the contour of the body each time at a different location, so that a contour point can be determined for each angular position.

Embodiments in accordance with the invention will be described in detail hereinafter, by way of example, with reference to the accompanying diagrammatic drawing.

Figure 2:
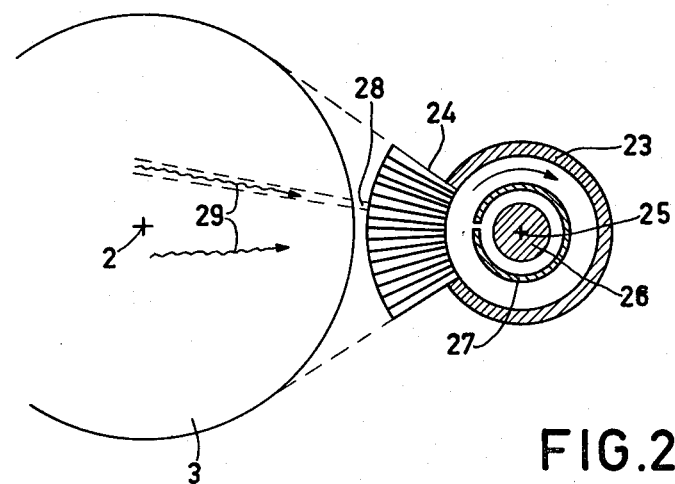
Figure 3:
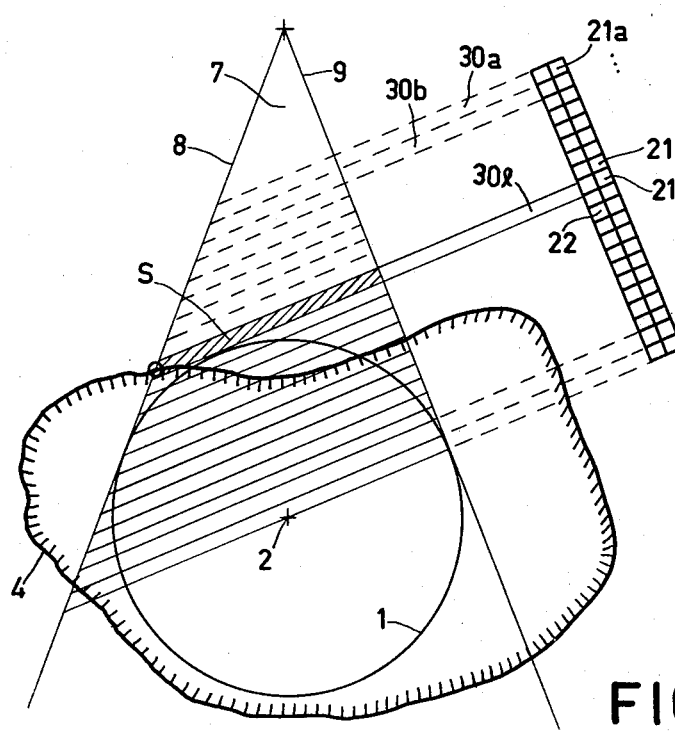
Figure 4:
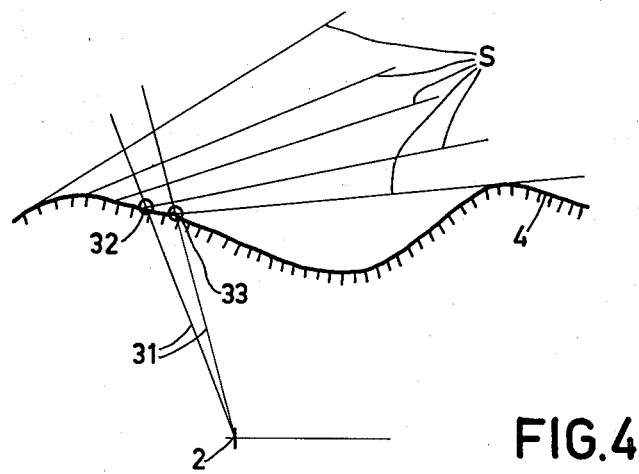
Figure 5:
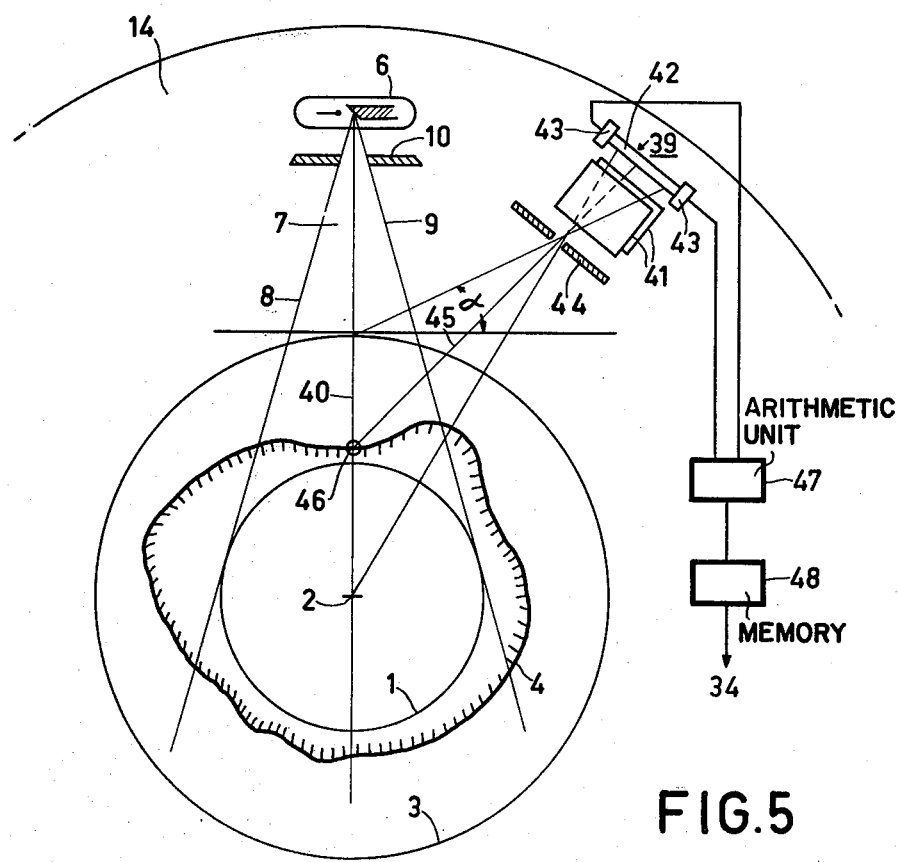

FIG. 1 shows an X-ray tomography apparatus, comprising an auxiliary detector device in accordance with the invention for measuring scattered radiation, FIG. 2 shows a further auxiliary detector device, FIG. 3 shows a circuit diagram in order to illustrate the method of determining the body contour, FIG. 4 shows a further circuit diagram for illustrating the method, and FIG. 5 shows an X-ray tomography apparatus comprising a further auxiliary detector device in accordance with the invention.

FIG. 1 diagrammatically shows an X-ray tomography apparatus. An examination zone 1 with a centre 2 is concentrically situated within a positioning zone 3. A patient 4 is positioned on an examination table 5 which is mounted on a base (not shown). An X-ray source 6 emits a flat, fan-shaped radiation beam 7 which extends in a plane which represents the examination plane and which is stopped by means of a diaphragm 10 so that the extreme rays 8 and 9 are tangential to the examination zone 1. The beam 7 irradiates the examination zone 1, or the body 4, and subsequently reaches a row 11 of separate detectors 12, each of which comprises collimators 13 in order to reduce the effect of scattered radiation on the measurements. The width of a detector 12 defines a beam path (not shown) of the fan-shaped radiation beam 7 which passes through the focus of the X-ray source 6. The X-ray source 6, the diaphragm 10 and the detector device 11 with the collimators 13 are mounted on a support 14 which is journalled to be rotatable, around an axis which extends through the centre 2 and perpendicularly to the plane of examination, in bearings 14a in a frame 14b, so that the radiation beam 7 can irradiate the examination zone 1 in any direction.

The logarithms of the transmission measuring values of the radiation measured by the detectors 12 are formed in a logarithm unit 15 and are subsequently stored in a memory 16. In a sorting device 17, the converted measuring values are resorted to form groups of measuring values along parallel beam paths which extend through the examination zone 1, and are subsequently used in an arithmetic device 18 for determining a two-dimensional absorption distribution in the examination zone 1 which can be displayed on a monitor 19.

Adjacent the radiation beam 7 there is arranged an auxiliary detector device 20 which is mounted on the rotatable support 14 and which consists of an array of separate detector elements 21 (for example, thirty elements) which comprise collimators 22. The collimators 22 are shaped so that only the scattered radiation which follows parallel scattered radiation paths (30a, 30b, see FIG. 3) passes therethrough and reaches the detector elements 21.

For example, a part 7a of the scattered radiation which extends parallel to the stopped radiation beam paths reaches a detector element 21, whilst another part 7b of the scattered radiation which is directed transversely of the scattered radiation paths is absorbed by the collimators 22. The collimators 22 can be made, for example, of a rectangular block of lead which is arranged in front of the detector elements 21 and which comprises a series of parallel bores, the distances therebetween corresponding to the distance between adjacent detector elements 21. Obviously, the lead block may also be shaped as an arc of a circle, so that it can be more readily mounted on the support 14. The detector elements 21 are arranged on an arc of a circle behind the block.

The length of the auxiliary detector device 20 is such that the scattered radiation paths associated with the extreme detector elements 21 are tangent to the positioning zone 3 or extend through the centre 2 of the examination zone 1. When the rotatable support 14 performs a complete rotation through 360° during the recording of the transmission measuring values, the said array of detector elements 21 suffices to record the scattered radiation in order to determine the contour of the body 4. When the support 14 is rotated only through 180°, the auxiliary detector device 20 must comprise approximately twice as many detector elements, so it must be twice as long, in order to cover the complete positioning zone by parallel scattered radiation paths. Alternatively, on the side of the radiation beam 7 opposite the auxiliary detector device 20 there may be provided a second auxiliary detector device which is similar to the auxiliary detector device 20 shown, so that the contour of the body 4 can be more accurately measured.

Each of the detector elements 21 may be composed of, for example, a sodium iodide scintillator and an associated photodiode, because on the accuracy of the measuring signal to be generated substantially less severe requirements are on them than on the measuring signals generated by the detectors 12.

Instead of the so-called third generation computer tomography apparatus shown in FIG. 1, use can be made of a fourth generation apparatus. The detectors 12 are then replaced by stationary detectors which are uniformly arranged within the circular zone of the frame 14b. Accordingly, the detector elements 21 can be replaced by groups of stationary detectors. The collimators 22, however, remain necessary for the stopping of the parallel scattered radiation paths which cover the positioning zone 3.

FIG. 2 shows a further embodiment of an auxiliary detector device. On the surface of a hollow cylinder 23 there are arranged a large number of laminations 24 which serve as collimators and which may be made of, for example, lead, each lamination being arranged in a plane containing the cylinder axis 25. These laminations stop scattered radiation paths which converge with respect to each other, the convergence point thereof being situated on the cylinder axis 25, and which cover the complete positioning zone 3. On the cylinder axis 25, extending perpendicularly to the examination plane, there is arranged a scintillation crystal 26 whereto a photomultiplier (not shown) is coupled. A slit diaphragm 27 which is rotatable around the scintillation crystal 26 and which allows passage to scattered radiation along only one separate radiation path 28 rotates at a speed of approximately 3000 revolutions per minute. The local resolution of the auxiliary detector device, and hence the accuracy of the determination of the position of a scattered X-ray 29, is thus given by the spacing of the laminations 24 and the width of the slit in the diaphragm 27.

The determination of the contour of the body 4 from the scattered radiation measuring values will be described with reference to the FIGS. 3 and 4. The explanation will be given on the basis of parallel scattered radiation paths; however, a similar explanation can be given for converging scattered radiation paths according to FIG. 2. A large number of parallel extending scattered radiation paths $30a$, $30b$, . . . etc., stopped on the basis of the detector elements 21, $21b$, . . . and their associated collimators 22 extend approximately transversely of the extreme ray 9 of the fan-shaped radiation beam 7. Scattered radiation can be determined along these scattered radiation paths by means of the detector elements $21i$. Because X-radiation is scattered to a high degree within the body, the detectors $21a$ to $21k$ will measure no or only little scattered radiation which is below a predetermined threshold. A substantial amount of scattered radiation is measured only as from the detector element $21l$. As will be described in detail hereinafter, with the scattered radiation path $30l$ on which scattered radiation is measured and which is situated furthest from the centre 2 of the examination zone 1 there is associated a path segment S whose position corresponds to that of the scattered radiation path $30l$. The length of the path segment S is limited by the extreme rays 8 and 9 of the fan-shaped radiation beam 7. Path segments for all directions of the radiation beam 7 through the examination zone 1 are thus successively determined.

When the examination zone position of the path segment S thus obtained is plotted in a two-dimensional diagram as shown in FIG. 4, it will be seen that part of the path segments S terminate at the body contour or are tangent to the body contour. The contour points of the body 4 are determined by points of intersection of the path segments S with vectors (straight lines) 31 which extend in different directions from the centre 2 of the examination zone 1 and which enclose a small angle with respect to each other. On a vector 31 a contour point of the body 4 is formed at the area where the distance between a point of intersection and the centre 2 is smallest. For example, the points of intersection 32 and 33 are contour points of the body 4.

FIG. 1 shows a block diagram for the electronic determination of the contour points. In a comparison unit 34, the scattered radiation measuring values produced by the detector elements 21 are compared with a threshold value which is chosen to be so high that low radiation intensities, for example, originating from the structural elements of the device, are not interpreted as being scattered radiation measuring values. On the output of the comparison unit 34 either a logic "1" or a logic "0" appears, depending on whether or not a sufficiently high scattered radiation intensity is measured. The detector output signals ("0" or "1") are stored in a memory 35 which comprises as many memory locations as there are distinct scattered radiation paths formed by the auxiliary detector device 20. In a further comparison unit 36, neighbouring memory locations are each time compared by means of an EXCLUSIVE-OR element. A transition of the output signals from "0" to "1" such as occurs, for example, for the detector elements $21k$ and $21l$ in FIG. 3, leads to an "1"-output of the EXCLUSIVE-OR element, so that the position of the scattered radiation paths, for example, $30l$ in FIG. 3 which is furthest from the centre 2 of the examination zone 1 is characterized. This position is stored in a further memory 37, together with the angular position of the support 14, given by a detector 140, with respect to the frame $14b$. An arithmetic unit 38 then determines the contour points of the body 4 in the described manner by means of the path segments S and the vectors extending through the centre 2 in different directions (for example, 31 in FIG. 4). Subsequently, the geometrical length values which have to be multiplied by a mean absorption coefficient of the body, for example, that of water are also calculated in the arithmetic unit 38, these values being used, together with the transmission measuring values along beam paths through the examination zone 1, for reconstructing the absorption distribution in the examination zone 1 by means of the arithmetic device 18.

FIG. 5 shows a further device for determining the body contour. The auxiliary detector device 39 is situated in a measuring plane which contains the symmetry line 40 of the fan-shaped radiation beam 7 and which encloses an angle ($\alpha$) of approximately 30° with respect to the examination plane. The symmetry line 40 of the fan-shaped radiation beam 7 is formed by the line which extends through the centre 2 of the examination zone 1 and through the focus of the X-ray source 6. Above and below the measuring plane, or parallel thereto, two diaphragm plates 41 are arranged one opposite the other in order to ensure that only the scattered radiation which extends in the measuring plane, and hence from the symmetry line 40, is incident on the auxiliary detector device 39. The auxiliary detector device 39 comprises, for example, a scintillator crystal 42 and a photomultiplier 43 at each end. For the imaging of the scattered radiation on the scintillation crystal 42 there is provided a slit diaphragm 44, the longitudinal direction of the slit therein extending perpendicularly to the measuring plane. Using the auxiliary detector device 39 and the diaphragms 41, 44, each point on the symmetry line 40 in the positioning zone 3 or, for example, only half the points on the symmetry line 40, as shown in FIG. 5, can be unambiguously imaged on the scintillation crystal 42. Scattered radiation originating from points outside the symmetry line 40 is absorbed, for example, by the diaphragm plates 41 which are made of lead, so that this scattered radiation is not detected.

Each point on the symmetry line 40 thus has unambiguously associated with it a given location on the surface of the scintillation crystal 42, so that by comparison of the output signals of the auxiliary detector device 39, the scattered radiation path 45 on which the scattered radiation intensity is high enough and which is situated furthest from the centre 2 of the examination zone 1 can be determined by means of the block diagram shown in FIG. 1 (elements 34 to 38). A contour point 46 of the body 4 is then formed as the point of intersection of this beam path 45 with the symmetry line 40. By rotation of the support 41 on which the radiation source 6 and the auxiliary detector device 39 and the diaphragms 41 and 44 are mounted, the symmetry line 40 can be made to cover any point of the contour of the body 4, so that all contour points required can be determined in the described manner.

In the auxiliary detector device shown in FIG. 5, comprising a scintillation crystal 42, the number of photons which is incident on a given measuring location on the scintillation surface is counted. For this purpose there is provided an arithmetic unit 47 which serves to determine the separate measuring locations from the output signals of the photomultiplier 43. The arithmetic unit 47 is also connected to a memory 48 which comprises a memory channel for each measuring location and which stores the number of photons arriving per measuring location. The memory 48 is connected to the elements 34 to 38 of FIG. 1 which are now of a digital type. Because the auxiliary detector device 39 has a resolution which is limited in time, it must be ensured that the counting periods of the total number of photons arriving on the scintillation crystal 42 is limited to approximately $10^6$/s. This can be achieved by choosing the slit of the diaphragm 44 to be sufficiently narrow.

The threshold comparator 34 of the device shown in FIG. 5 can be replaced by a differentiating member. It will be clear that the scattered radiation path 45 can also be determined by the formation of difference quotients. However, it will then be problematic to determine a correct threshold value for the suppression of the effects of scattered radiation produced outside the body. The major advantage, however, consists in that the differentiation of the scattered radiation measuring values associated with the various scattered radiation paths enables even more pronounced absorption differences along the symmetry line 40 to be found, for example, such as those originating from air inclusions in the body 4. When the measuring system is rotated, for example, through 360°, all air inclusions are thus found, including those which are situated outside the examination zone 1 and which thus far could not be taken into account for the determination of the absorption distribution. The arithmetic unit 38, therefore, is extended and now multiplies, for example, parts of the length of the symmetry line 40 which are assumed to extend through water, for example, by the absorption coefficient of water; from the values thus obtained, this unit subtracts the values which are produced by multiplication of parts of the length of the symmetry line 40 through the air inclusions by the absorption coefficient of air. The corrected values thus obtained are very useful, for example, when the plane of examination extends through the area of the lungs of a human body and lead to a higher accuracy of the reconstructed absorption distribution in the examination zone 1. The comparison element 37 can be dispensed with in this embodiment.

The auxiliary detector device 39 with the scintillation crystal 42 and the photomultipliers 43 can also be replaced by a large number of separate detector elements. The elements 47 and 48 can then be dispensed with. Furthermore, the slit diaphragm 44 and the auxiliary detector device 39 may be replaced by an auxiliary detector device 20 as shown in FIG. 1 with the associated collimators 22 for the formation of parallel scattered radiation paths if they are combined with the diaphragm plates 41.

When the body contour is only partly determined by means of the method, the body contour situated opposite this part can be determined so that on beam paths which extend through the already determined part of the body contour and through the examination zone there is each time determined a new contour point of the body whose distance from the already determined contour point is measured as a value which corresponds to the quotient of each time the absorption value associated with the beam path and measured by measurement of the body absorption and a preselected mean absorption coefficient. Further parts of the body contour can thus be at least approximately determined (see German Patent Application P 28 44 927.6).

What is claimed is:

1. A method of determining contour points of a body in a positioning zone of an examination plane comprising the steps of:
    completely irradiating an examination zone which is enclosed within the positioning zone from a plurality of different directions with a flat beam of X-rays which lies in the examination plane and is fan-shaped therein;
    for each of the plurality of directions, measuring radiation which is scattered out of the fan beam by the body along a plurality of measuring paths, which paths intersect the fan beam, cover at least one-half of the positioning zone adjacent a center situated therein, and do not overlap each other within the positioning zone;
    for each of the plurality of directions, selecting, from among the plurality of measuring paths, a path along which a predetermined minimum amount of scattered radiation has been measured and which is furthest from the center;
    recording the position of the segments of the selected paths which are within the fan-shaped beam; and
    determining the points of intersections of the recorded segment positions with each of a plurality of straight lines which pass through the center and selecting as a contour the point of intersection on each line which is closest to the center.

2. The method of claim 1 wherein the scattered radiation paths cover approximately the entire positioning zone.

3. A method of determining contour points of a body in a positioning zone of an examination plane comprising the steps of:
    completely irradiating an examination zone which is enclosed within the positioning zone from a plurality of different directions with a flat beam of X-rays which lies in the examination plane and is fan-shaped therein;
    measuring X-rays scattered from the fan-shaped beam by the body in a measuring plane which encloses an angle with respect to the examination plane and intersects the examination plane to define a single beam path which passes through the source of the beam by stopping the scattered X-rays so that an unambiguous relationship is established between adjacent points on the beam path and adjacently extending scattered radiation paths in the measuring plane which extend through those points detecting the scattered radiation along the adjacently extending paths; and
    comparing output signals produced by said detection to determine the position of the contour points.

4. The method of claim 1 or 3 wherein the scattered radiation paths extend in parallel directions.

5. The method of claim 1 or 3 wherein the scattered radiation paths converge at a point of convergence which is outside of the positioning zone.

6. The method of claim 3 wherein scattered radiation is only measured from points on one side of a center of the examination zone.

7. The method of claim 3 wherein the measuring plane encloses an angle of approximately 30° with respect to the examination plane.

8. X-ray apparatus for examining a body comprising:
X-ray source means which function to project a fan-shaped beam of radiation through an examination zone in an examination plane from a plurality of different directions;
auxiliary detector means, comprising a plurality of X-ray detection positions which are adjacently disposed in the examination plane, which function to measure auxiliary radiation which is scattered outside of the radiation beam from points in a positioning zone which encloses the examination zone;
collimator means disposed between the auxiliary detector means and the positioning zone which function to selectively absorb radiation to define a plurality of scattered radiation paths which do not overlap within the examination zone and which cover at least one-half of the positioning zone adjacent a center thereof, each of which paths extend from a detector position through the positioning zone, and
electronic computer means connected to receive signals from the detector means which function to determine the contour of the body in the examination plane from output signals thereof.

9. The device as claimed in claim 8 wherein the collimator means function to define parallel scattered radiation paths.

10. The device of claim 8 wherein the collimator means function to define radiation paths which converge at a point outside of the positioning zone.

11. The device of claim 8 wherein the collimator means comprise a large plurality of planar laminations which define the detector positions and which are disposed on the surface of a hollow cylinder in planes which extend through the cylinder axis, the cylinder extending perpendicular to the examination plane, and rotating slit collimator means disposed within the cylinder concentric to the axis thereof; and wherein the auxiliary detecting means comprise a detection element disposed within the rotating slit collimator means so that the rotating slit collimator means function to successively conduct scattered radiation to the element from a plurality of radiation paths which are defined by the laminations.

12. X-ray apparatus for examining a plane of a body which is disposed within a positioning zone comprising:
X-ray source means which function to project a fan-shaped beam of radiation in an examination plane from a plurality of different directions through an examination zone which is enclosed within the positioning zone;
auxiliary detector means disposed outside of the examination plane for measuring radiation, which is scattered from the fan-shaped beam within a positioning zone into a measuring plane, the measuring plane being oriented so that it encloses an angle with respect to the examination plane and the line of intersection of the measuring plane and the examination plane defines a beam path which passes through the X-ray source means;
collimating means which selectively absorb radiation and function so that only radiation which is scattered by the body from the beam path is detected by the auxiliary detecting means; and
an electronic computer which functions to determine contour points of the body in the examination plane from output signals of the auxiliary detector means.

13. A device as claimed in claim 12 further comprising second collimator means which function to selectively absorb radiation so that only scattered radiation from a desired part of the beam path impinges on the auxiliary detector means.

14. The device of claim 13 wherein the second collimator comprises a slit diaphragm which defines a slit having a longitudinal direction which extends perpendicular to the measuring plane.

15. A device as claimed in claim 12 wherein the first collimator means comprises two parallel radiation absorbing plates disposed on opposite sides of the measuring plane and parallel to the beam path.

16. The device as claimed in claim 12 wherein the auxiliary detector means comprises a scintillation crystal and two photomultipliers which are situated on opposite ends of the crystal.

17. The device as claimed in claim 12 wherein the auxiliary detector means comprises a plurality of separate, adjacently disposed detector elements.

* * * * *